(12) United States Patent
Griggs (10) Patent No.: US 8,034,054 B2
(45) Date of Patent: Oct. 11, 2011

(54) INTRAMEDULLARY BONE DEVICE (76) Inventor: Ian Ross Griggs, Warrandyte South (AU)

( * ) Notice: Subject to any disclaimer, the term of this patent is extended or adjusted under 35 U.S.C. 154(b) by 206 days.

(21) Appl. No.: 11/883,072

(22) PCT Filed: Jan. 31, 2006

(86) PCT No.: PCT/AU2006/000114
§ 371 (c)(1),
(2), (4) Date: Jul. 26, 2007

(87) PCT Pub. No.: WO2006/079184
PCT Pub. Date: Aug. 3, 2006

(65) Prior Publication Data
US 2008/0312657 A1    Dec. 18, 2008

(30) Foreign Application Priority Data
Jan. 31, 2005 (AU) ................ 2005900388

(51) Int. Cl.
*A61B 17/72* (2006.01)
(52) U.S. Cl. .......................... 606/63; 606/66
(58) Field of Classification Search ............ 606/60, 606/62–68, 88, 92–95; 623/20.14–20.31, 623/20.35–20.36, 22.4
See application file for complete search history.

(56) References Cited

U.S. PATENT DOCUMENTS

| 3,374,786 | A | * | 3/1968 | Callender, Jr. ............ 606/65 |
| 4,262,665 | A | * | 4/1981 | Roalstad et al. ............ 606/62 |
| 5,057,103 | A | * | 10/1991 | Davis ............................ 606/63 |
| 5,074,882 | A | * | 12/1991 | Grammont et al. ........... 606/63 |
| 5,263,955 | A | * | 11/1993 | Baumgart et al. ............. 606/63 |
| 5,575,790 | A | * | 11/1996 | Chen et al. ..................... 606/60 |
| 5,578,035 | A | * | 11/1996 | Lin .................................. 606/68 |
| 5,658,287 | A | * | 8/1997 | Hofmann et al. .............. 606/63 |
| 5,855,579 | A | * | 1/1999 | James et al. .................... 606/62 |
| 5,879,352 | A | * | 3/1999 | Filoso et al. .................... 606/62 |
| 6,077,264 | A | | 6/2000 | Chemello |
| 6,447,513 | B1 | * | 9/2002 | Griggs .......................... 606/62 |
| 6,488,684 | B2 | | 12/2002 | Bramlet et al. |
| 6,491,696 | B1 | * | 12/2002 | Kunkel ...................... 606/105 |
| 6,926,719 | B2 | * | 8/2005 | Sohngen et al. .............. 606/64 |

FOREIGN PATENT DOCUMENTS

| EP | 0 922 437 | 6/1999 |
| WO | WO 96/39584 | 12/1996 |
| WO | WO 98/51228 | 11/1998 |
| WO | WO 00/25690 | 5/2000 |
| WO | WO 2004/026158 | 4/2004 |

* cited by examiner

*Primary Examiner* — Eduardo C Robert
*Assistant Examiner* — Lynnsy Schneider
(74) *Attorney, Agent, or Firm* — Stein McEwen, LLP (57) ABSTRACT

An intramedullary bone device comprises a distal outer member, a proximal outer member for positioning in substantial axial alignment with the distal outer member, the distal and proximal outer members each having at least one opening in a wall thereof. The distal outer member and the proximal outer member each have a passage therein. The device also has a distal inner member sized to be slideably received within the passage of the distal outer member and a proximal inner member sized to be slideably received within the passage of the proximal outer member. An extender/retractor is able to selectively extend or retract to selectively lengthen or shorten, respectively, the device. The device has pins movable between a retracted position and an extended position, wherein the pins extend through the at least one opening in the distal and proximal outer members to fix the device to a bone during use.

22 Claims, 9 Drawing Sheets

INTRAMEDULLARY BONE DEVICE

The present invention relates to an intramedullary bone device. More specifically, the present invention relates to an intramedullary bone device of the kind in which the length of the device can be selectively increased or decreased.

BACKGROUND TO THE INVENTION

Fixation and stabilisation of fractures can be difficult, especially in long bones. Two techniques are normally used. The first technique involves placing a plate on one side of the bone and screwing the plate to the bone on either side of the fracture with a plurality of screws. This technique suffers from the disadvantage that forces are applied to the bone via the screws from one side of the bone only, which can cause uneven loading on the bone.

The second technique for fixation and stabilisation of fractures involves inserting an intramedullary pin into the medullary canal of the bone. Fixation pins may or may not be used. If fixation pins are not used, the bone at either side of the fracture may rotate around the intramedullary pin which leads to misalignment of the bone. If fixation pins are used, it is necessary to drill holes through the bone on either side of the fracture and insert fixation pins through the holes in the bone with those in the intramedullary pin, thereby complicating the operative procedure and potentially causing an increase in post-operative recovery time for the patient.

Fixation of prosthesis, such as artificial hips and artificial knees, also faces similar difficulties. For example, fitting an artificial hip to a patient typically involves preparing the upper part of the femur and inserting a stem portion of the hip prosthesis into the medullary canal of the femur. The stem is fixed to the femur by bone cement or by inserting external pins through holes drilled through the femur and into and through holes in the stem portion of the artificial hip. The difficulties with using external pins have been discussed above. In cases where bone cement is used, misalignment and shifting of the prostheses can occur if the cement does not adequately adhere to the bone.

My Australian patent no. 755111 describes an intramedullary bone fixation device which uses a plurality of extendable pins to fix the device to the bone. In use of this device, the device is inserted into the medullary canal of a bone and the pins extended such that they extend into the bone surrounding the medullary canal to thereby fix the device to the bone. The entire contents of my Australian patent no. 755111 are herein incorporated by cross-reference.

FIG. 13 of my Australian patent no. 755111 shows an intramedullary bone fixation device that is of expandable length. This device includes an inner member having first and second portions and an outer member having first and second portions. The first portion of the inner member includes a bore having a threaded portion. A bore is also included in the second portion of the inner member, with the bore of the second portion terminating in a blind end. A screw is threadably inserted into the bores of the inner member pieces. When the screw has been fully inserted, the end of the screw strikes the blind end. Further rotation of the screw then acts to expand the length of the inner member by pushing apart the two portions of the inner member. As the pins have been inserted into the bones surrounding the medullary canal, extending the length of the inner member also extends the length of the outer member. The device shown in FIG. 13 of my earlier Australian patent number 755111 is used by pre-setting the device at a desired length. However, once the length of the device has been set, it is a static device. The screw locks the proximal and distal components in the desired pre-set position.

The device shown in FIG. 13 of my earlier Australian patent no. 755111 can suffer from the following problems:

a) the screw can become stuck when it contacts the end of the blind bore in the second part of the inner member. This problem is exacerbated by the threaded screw being in threaded engagement with the bore in the second member and the combination of the threaded engagement and contact with the blind end of the bore making it very difficult, if not impossible, to further turn the screw; and b) the device shown in FIG. 13 of my earlier Australian patent no. 755111 is not able to shorten the length of the device because turning the screw in the opposite direction simply unscrews the screw from the threaded bores.

My earlier international patent application no. PCT/AU0301207, published as WO 2004/026158, relates to fixation devices which include pins that can be moved from a retracted to an extended position. The entire contents of my earlier international patent application no. PCT/AU03/01207 are also incorporated herein by cross-reference.

The applicant does not concede that the prior art discussed herein forms part of the common general knowledge in this art in Australia.

Throughout this specification, the terms "comprising" and its grammatical equivalents are to be taken to have an inclusive meaning unless the context indicates otherwise.

The applicant does not concede that the prior art discussed in this specification forms part of the common general knowledge in Australia or any other country.

BRIEF DESCRIPTION OF THE INVENTION

In a first aspect, the present invention provides an intramedullary bone device comprising a distal outer member having at least one opening in a wall thereof, a proximal outer member for positioning in substantial axial alignment with the distal outer member, the proximal outer member having at least one opening in a wall thereof, said distal outer member having a passage therein, said proximal outer member having a passage therein, a distal inner member sized to be slideably received within the passage of the distal outer member, a proximal inner member sized to be slideably received within the passage of the proximal outer member, extension/retraction means being selectively operable to selectively alter the relative longitudinal positioning between the distal inner member and the proximal inner member, said extension/retraction means being able to selectively extend or retract to selectively lengthen or shorten, respectively, the device, and pins movable between a retracted position and an extended position, wherein the pins extend through the at least one opening in the distal and proximal outer members to fix the device to a bone during use.

The device in accordance with the present invention includes an extension/retraction means for selectively lengthening or shortening the device, either prior to or after the device has been implanted. The device allows for lengthening or shortening (suitably intermittent lengthening or shortening) after the device has been implanted. Most suitably, the relative axial orientation of the extended pins in both the proximal and distal components of the device is maintained during lengthening or shortening.

Preferably, the extension/retraction means is freely rotatable relative to one of the proximal or distal inner members and operates such that rotation alters the relative longitudinal position of the other of the proximal or distal inner members.

Even more preferably, the extension/retraction means is freely rotatable relative to one of the proximal or distal inner members whilst retaining its longitudinal position relative to that inner member, and rotation of the extension/retraction means alters the relative longitudinal position between the extension/retraction means and the other of the proximal or distal inner members.

Most preferably, the extension/retraction means comprises a screw or bolt having a threaded shank threadably engaged with the distal inner member and a head positioned within a complementarily shaped recess in the proximal inner member such that the head can rotate relative to the proximal inner member and resist removal from the recess by application of a longitudinal force.

Instead of a screw and thread arrangement, the extension/retraction means and the distal inner member may be provided with an appropriate projection and groove arrangement, interengaging ramps, or any other arrangement that causes longitudinal movement between the extension/retraction means and the distal inner member upon rotation of the extension/retraction means.

In a preferred embodiment, the extension/retraction means comprises the screw described above and the head defines at least one shoulder that engages with an opposed shoulder formed in the recess of the proximal inner member. Alternatively, the head may included at least one neck region of reduced diameter that engages with a complementary shaped projection in the recess in the proximal inner member. As a further alternative, the head may included a region of increased size relative to the shank, which region of increases size fits within a complementary shaped region in the recess.

Preferably, the recess in the proximal inner member includes a shank receiving portion and a head receiving portion.

Preferably, the proximal inner member includes a passage extending therethrough. In this fashion, a tool can be inserted into the proximal inner member to engage with the extension/retraction means to thereby rotate the extension/retraction means. Alternatively, the extension/retraction means may have a head located at one end of the proximal inner member and the shank extends through the proximal inner member into engagement with the distal inner member. In this fashion, the head of the extension/retraction means is located at or near the proximal end of the proximal inner member to provide access for selective operation of the extension/retraction means.

Preferably, the distal inner member and the proximal inner member are arranged such that relative rotational movement therebetween is avoided. For example, in one embodiment, one of the proximal or distal inner members may be provided with a flat land that engages with a projection extending from the other of the proximal or distal inner members. More preferably, one of the proximal or distal inner members is provided with two flat lands that engage with two projections extending from the other. Engagement between the projections and flat lands stops relative rotation between the proximal and distal members.

As a further alternative, one of the proximal or distal inner members could include a keyway (or more than one keyway) that engages with a key (or more than one key) formed on the other of the proximal or distal inner members.

It is also preferred that the proximal and distal outer members are arranged such that relative rotational movement therebetween is avoided. Suitably, the proximal and distal outer members have one or more tongues that interfit with complementary tongues on the other of the proximal or distal outer members. Most preferably, the proximal outer member has two tongues extending from an end that interlock with two tongues extending from the distal outer member to thereby prevent relative rotation therebetween.

The device in accordance with the present invention also includes a plurality of pins that can move between a retracted position and an extended position. Suitably, in the retracted position, the pins do not extend beyond an outer surface of the outer members.

In the extended position, the pins extend through the one or more openings in the walls of the outer members and into the bone surrounding the medullary canal. In this fashion, the pins extend into the bone to thereby fix the device to the bone.

The pins may be arranged as described in my earlier Australian patent no. 755111. For example, the pins may be arranged in transverse grooves on the inner members. Rotation of the inner members relative to the outer members causes the pins to extend through the openings in the outer members and into the bone surrounding the medullary canal.

The pins may also be arranged as described in my earlier international patent application no. PCT/AU03/01207, WO 2004/026158.

In one embodiment, at least one pin extends across a passage extending through the proximal inner member when the pin is in the retracted position. In this fashion, insertion of a tool through the passage of the proximal inner member is prevented as the tool would strike the pin extending across the passage. When the pin is moved to the extended position, the pin no longer extends across the passage in the proximal inner member, thereby allowing a tool to be inserted along the passage to operate the extension/retraction means. In this fashion, the extension/retraction means can only be operated when the pins have been moved to the extended position, such as by moving the pins to the extended position prior to insertion into a bone cavity so as to allow the length of the device to be adjusted as desired followed by retraction of the pins and insertion into the bone cavity or by the device being fixed to the bone surrounding the medullary canal by extending the pins. It will also be appreciated that other embodiments of the invention do not require the pins to extend across the passage when in the retracted position. In such cases, adjustment of the length of the device can be made at any time, whether the pins are in the retracted or extended position.

The person skilled in the art will also appreciate that there may be a number of other mechanisms that can be used to move the pins from the retracted to the extended position. The present invention encompasses all such pin mechanisms known to a person skilled in the art.

In a second aspect, the present invention provides a method for using a device in accordance with the first aspect of the present invention, the method including the steps of inserting the device into a medullary canal of a bone, moving the pins to an extended position to thereby fix the device to the bone surrounding the medullary canal such that the distal members are fixed to the bone on one side of a break in the bone and the proximal members are fixed to the bone on another side of a break in the bone, and selectively lengthening or shortening the device by operation of the extension/retraction means.

The ability to shorten the device in accordance with the present invention is particularly useful in that when the bones are aligned and the device inserted and the pins extended, the device can then be shortened (or contracted) to give compression of the bones at the fracture site, which is very desirable to aid in fracture repair.

The ability of the device to lengthen is particularly useful in situations where there is a deficit of bone. For example, in the condition of hemi facial microsomia, articulation of the jaw has not formed properly in children. The device of the present invention can be used to treat this condition by operating on the jaw to cut a piece of bone near the area of articulation to separate that from the body of the jaw. The device in accordance to the present invention is inserted through the body of the jaw and into the fragment of bone that has previously been separated. The pins are then extended so that they attach to the body of the jaw and the fragment of bone. Then gradually, preferably twice a day, the fragment can be separated from the body of the jaw by slowly lengthening the length of the device, in a fashion that maintains a viable blood clot and hence bone healing capability, until the fragment moves into the area of normal jaw articulation. The device can then be left at that length until the bones heal and proper jaw articulation is provided.

DETAILED DESCRIPTION OF THE DRAWINGS

It will be appreciated that the drawings have been provided for the purpose of illustrating preferred embodiments of the present invention. Thus, it will be understood that the present invention should not be considered to be restricted to the particular embodiments shown in the drawings;

The intramedullary bone device in accordance with preferred embodiments of the present invention includes the following components:
distal outer member
proximal outer member
distal inner member
proximal inner member
an extension/retraction screw or bolt
fixation pins The above components are assembled together to provide an intramedullary bone device that can be fixed to the bone surrounding the medullary canal and subsequently be lengthened or shortened (contracted) if desired or required by the particular condition being treated.

Figure 1:
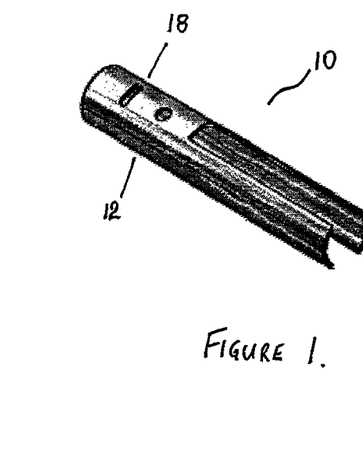
FIG. 1 shows a perspective view of a distal outer member in accordance with an embodiment of the present invention.
Figure 2:
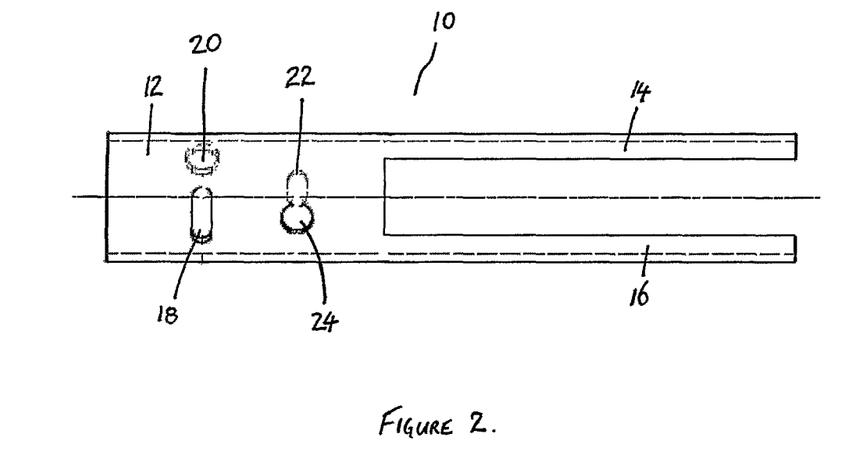
FIG. 2 shows a side view of the distal outer member shown in FIG. 1.
Figure 3:
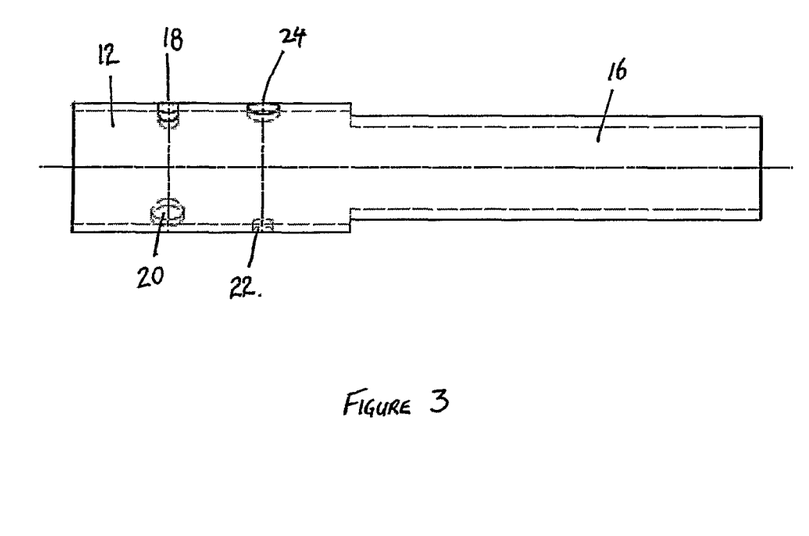
FIG. 3 shows another side view (rotated by 90° to that shown in FIG. 2) of the distal outer member shown in FIG. 1.

FIGS. 1-3 show various views of a distal outer member 10 suitable for use in an embodiment of the present invention. The distal outer member 10 is generally cylindrical in shape. The distal outer member 10 is hollow.

The distal outer member 10 includes a cylindrical body portion 12 having two projecting tongues 14, 16 extending therefrom. The distal outer member 10 further includes a first slot 18 that is in substantial longitudinal alignment with a further opening 20. A second slot 22 is in substantial longitudinal alignment with a further opening 24. The functioning of the slots and openings will be described hereunder.

Figure 4:
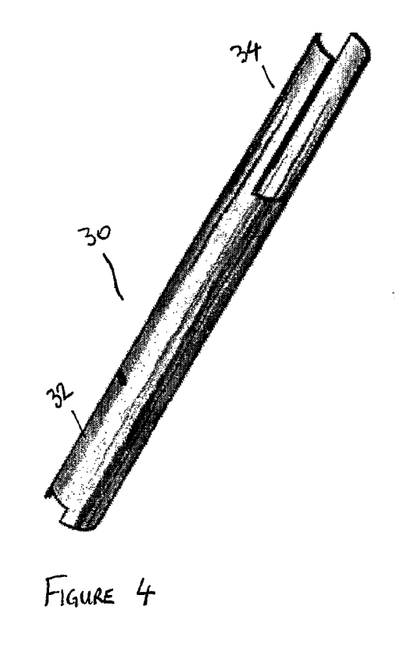
FIG. 4 shows a perspective view of a proximal outer member for use in an embodiment of the present invention.
Figure 5:
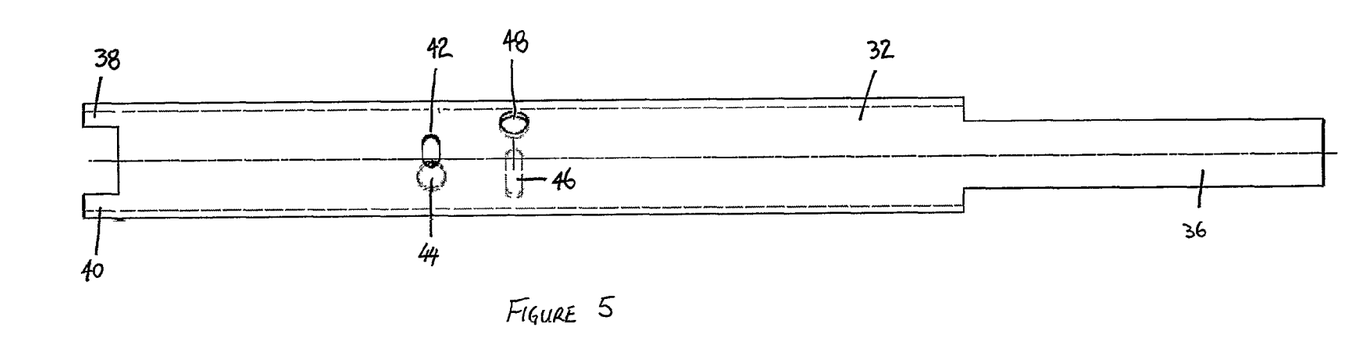
FIG. 5 shows an end view of the proximal outer member shown in FIG. 4.
Figure 6:
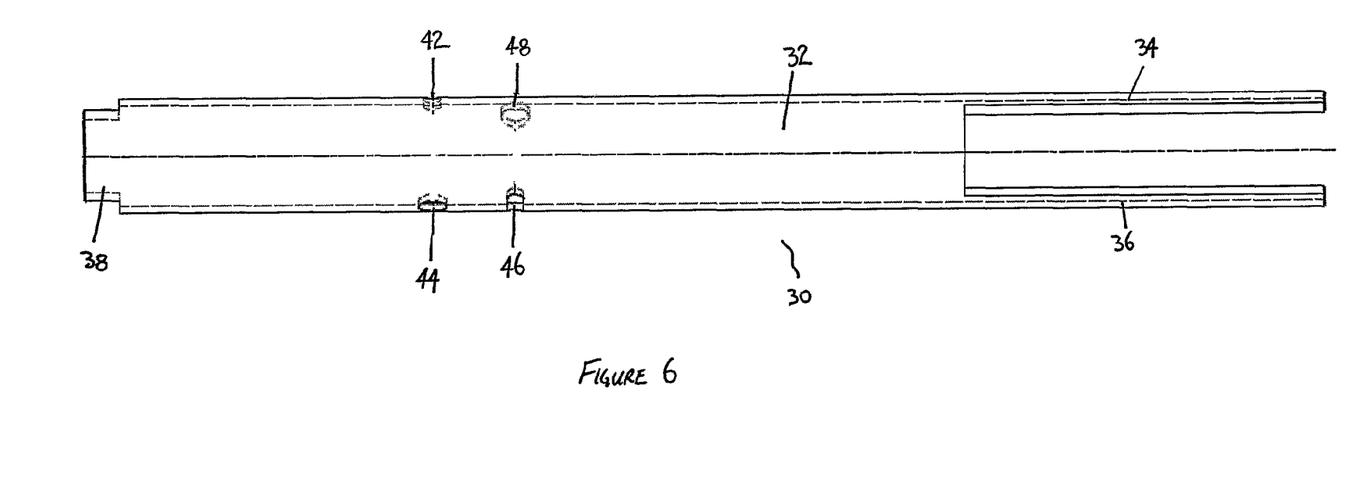
FIG. 6 shows another end view (rotated by 90° to that shown in FIG. 5) of the proximal outer member shown in FIG. 4.

FIGS. 4-6 show a proximal outer member 30 suitable for use in an embodiment of the present invention. The proximal outer member 30 includes a generally cylindrical body portion 32. Two projecting tongues 34, 36 extend from one end of the generally cylindrical body portion 32. Short projecting tongues 38, 40 extend from the other end of generally cylindrical body portion 32.

The generally cylindrical body portion 32 includes a first slot 42 that is in substantial longitudinal alignment with opening 44. Similarly, a second slot 46 is in generally longitudinal alignment with a further opening 48.

The tongues 34, 36 on the proximal outer member are sized and spaced such that they neatly interfit and interlock with the projecting tongues 14, 16 of the distal outer member 10. In this fashion, the distal outer member and proximal outer member can be fitted together such that they form a congruent outer tube. Rotation between the distal outer member and the proximal outer member is also avoided. It would be appreciated that the distal outer member and the proximal outer member are both hollow.

Figure 7:
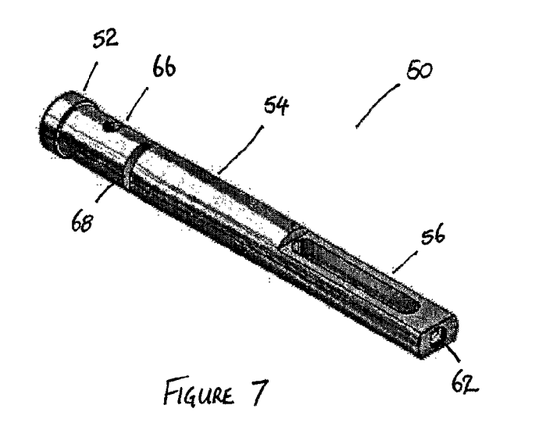
FIG. 7 shows a perspective view of a distal inner member for use in an embodiment of the present invention.
Figure 8:
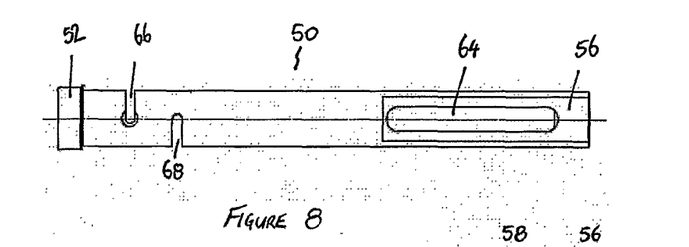
FIG. 8 shows a side view of the distal inner member shown in FIG. 7.
Figure 9:
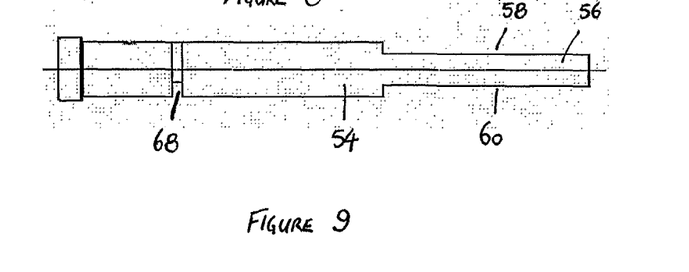
FIG. 9 shows another side view (rotated by 90° to that shown in FIG. 8) of the distal inner member shown in FIG. 7.
Figure 10:
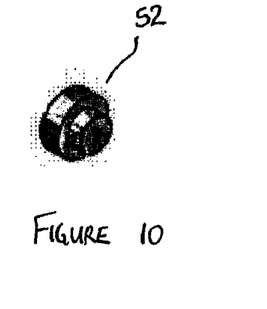
FIG. 10 shows a perspective view of an end button for joining to the distal inner member shown in FIGS. 7 to 9.
Figure 11:
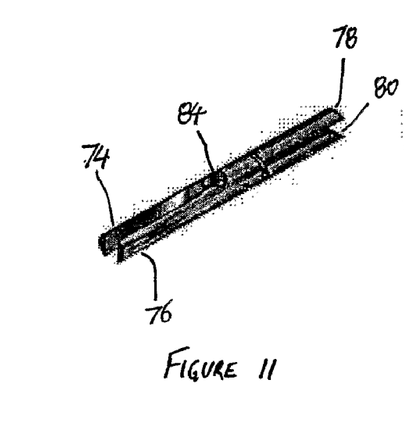
FIG. 11 shows a perspective view of a proximal inner member for use in an embodiment of the present invention.

FIGS. 7-9 show a distal inner member 50 suitable for use in the present invention. Distal inner member 50 is fitted at one end with a button 52. FIG. 10 shows detail of the button.

The distal inner member 50 comprises a generally cylindrical portion 54. A tongue 56 projects from one end. The tongue 56 is provided with two flat lands 58, 60. The end of tongue 56 has a threaded passage 62 formed therein. The tongue 56 further includes a slot 64 extending through a large extent of the tongue 56.

The generally cylindrical portion 54 of distal inner member 50 is suitably a solid generally cylindrical portion. It is provided with two transversely extending grooves 66, 68. As best shown in FIGS. 7 and 8, transversely extending grooves 66, 68 have a depth that is slightly larger than half the thickness of generally cylindrical portion 54. Transversely extending grooves 66, 68 are used to receive pins (not shown) that are used to fix the device to the bone surrounding the medullary canal. In particular, the pins operate in a manner similar to that shown in FIG. 15 of my earlier Australian patent no. 755111, the entire contents of which are herein incorporated by cross-reference.

FIGS. 11-14 show various views of a proximal inner member that is suitable for use in embodiments of the present invention. The proximal inner member 70 includes a generally cylindrical portion 72 has tines 74, 76 extending from one end thereof. Short tines 78, 80 extend from the other end of generally cylindrical portion 72.

Figure 14:
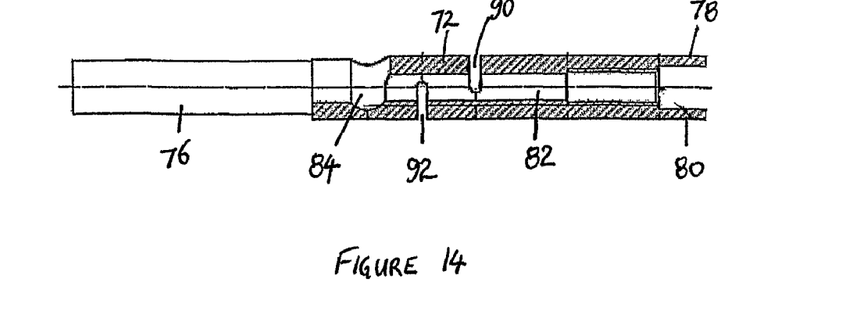
FIG. 14 shows a side view, partly in cross-section (and rotated by 90° to the view shown in FIG. 13) of the proximal inner member shown in FIGS. 11 and 12.

As shown in FIG. 14, generally cylindrical portion 72 is hollow and includes a passage 82 extending therethrough.

The distal end of passage 82 opens into recess 84, which recess is open at an upper side of generally cylindrical portion 72. Recess 84 includes an enlarged generally spherical portion 86 which is complementary in shape to the head of a screw or bolt (to be described with reference to FIGS. 15 and 16). The recess 84 further includes a shank receiving portion 88 of the screw shown in FIGS. 16 and 17.

The generally cylindrical portion 72 includes two transversely extending grooves 90, 92. Transversely extending grooves 90, 92 are arranged in a similar fashion to transversely extending grooves 66, 68 on the distal inner member 50. Transversely extending grooves 90, 92 also receive fixing pins and operate as shown with reference to FIG. 15 of my earlier Australian patent no. 755111. It will be appreciated that transversely extending grooves 90, 92 extend through the outer wall of generally cylindrical portion 72.

Figure 15:
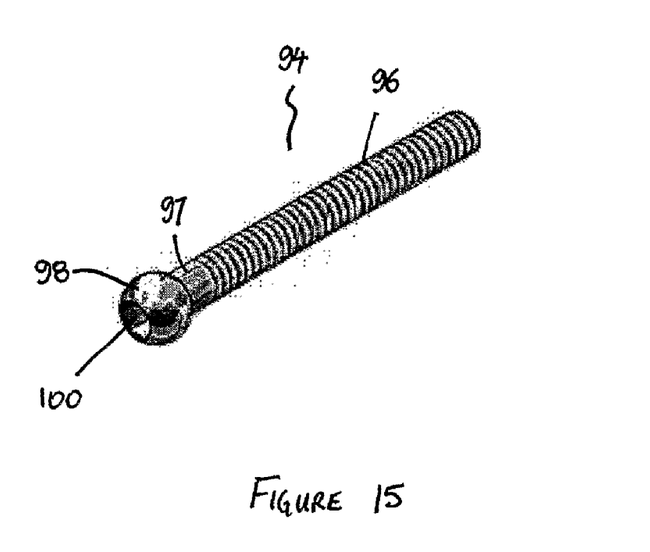
FIG. 15 shows a perspective view of a screw for use as the extension/retraction member in an embodiment of the present invention.
Figure 16:
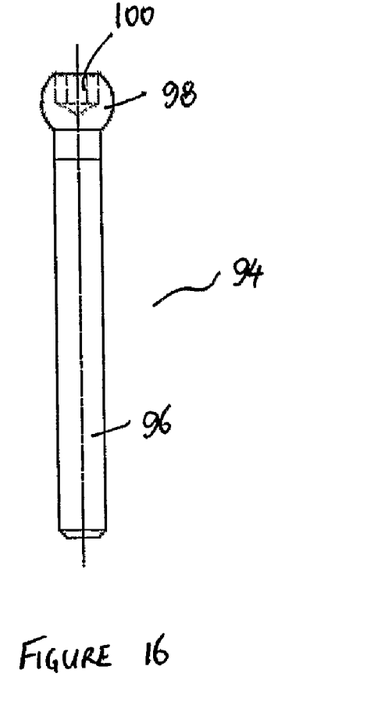
FIG. 16 is a side view of a screw shown in FIG. 15.

FIGS. 15 and 16 show a screw or bolt 94 that is suitable for use in some embodiments of the present invention. The screw or bolt 94 includes a threaded shank 96 and a generally spherical head 98. Generally spherical head is enlarged relative to the diameter of shank 96. The generally spherical head 98 and threaded shank 96 are sized such that they can be received in the enlarged generally spherical portion 86 and shank receiving portion 88, respectively of recess 84 in proximal inner member 70.

The screw or bolt 94 includes a hexagonal opening 100 in its proximal end. Hexagonal opening 100 is designed to engage with an allen key in order to enable the screw or bolt 94 to be rotated.

It will be appreciated that the screw or bolt 94 may be provided with any other mechanism that allows it to be engaged with a tool to enable the tool to be operated to rotate the screw or bolt 94. For example, the head 98 of the screw or bolt 94 may be provided with a slot or a philips head opening for receiving the end of a screwdriver. It may even be provided with a shaped projection designed to engage with an appropriately shaped socket connection of a tool.

In operation of the intramedullary device in accordance with an embodiment of the present invention, the screw 94 is positioned within the proximal inner bar such that the generally spherical head 98 of screw 94 rests in generally spherical portion 86 of recess 84. A non-threaded part 97 of the shank is received in shank receiving portion 88 of recess 84. In this fashion, it will be appreciated that the screw or bolt 94 can freely rotate whilst it is positioned in recess 84. However, due to the shape of the enlarged spherical head 98 in screw or bolt 94 and due to the complementary shape of the recess 84, applying a longitudinal force to the screw or bolt 94 cannot cause removal of the screw or bolt 94 from the recess 84. Thus, the longitudinal positioning of the screw or bolt 94 relative to the proximal inner member 70 is maintained even whilst the screw or bolt 94 is rotated.

The threaded shank 96 of screw or bolt 94 is initially screwed into threadable engagement with the threaded opening 62 in distal inner member 50. Once the screw or bolt 94 has been screwed into the threaded passage 62 to the desired extent, the distal inner member 50 is positioned relative to the proximal inner member 70 such that flat lands 58, 60 lie within and abut projections 74, 76. As the tongue 56 of distal inner member 50 is inserted between tines 74, 76, it will be appreciated that the spherical head 98 of screw or bolt 94 will be received in recess 84.

Due to the size and spacing of the projections 74, 76 relative to the size of the tongue 56, relative rotation between the distal inner member 50 and proximal inner member 70 is not possible.

Further assembly of the device requires that the distal outer member and proximal outer member are slidably positioned over the respective distal inner member and proximal inner member. The tongues 14, 16 of the distal outer member 10 are received in the spaces between the tongues 34, 36 of the proximal outer member 30 such that the distal outer member and proximal outer member form a congruent tube.

Suitably, the slot 18 and associated opening 20 of the distal outer member 10 are placed into alignment with the groove 66 in the distal inner member 50. Similarly, slot 22 and associated opening 24 are placed in alignment with groove 68 in the distal inner member 50. Likewise, the slot 42 and associated opening 44 are placed into alignment with groove 92 of the proximal inner member. Likewise, slot 46 and associated opening 48 of proximal outer member 30 are placed into alignment with transversely extending groove 90 of proximal inner member 70.

Figure 19:
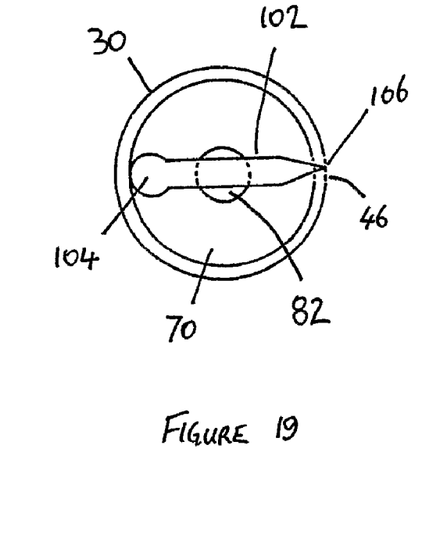
FIG. 19 is a cross-sectional end view showing a pin loaded in the device but in the retracted position.

The fixing pins are then loaded into the grooves in the inner members by passing the pins through openings 20, 24, 44 and 48. One such pin is shown in FIG. 19. In FIG. 19, which is a cross-sectional end view taken across groove 90, the pin 102 includes a generally spherical enlargement 104 at one end and a point 106 at the other end.

FIG. 19 shows pin 102 in a retracted position. As can be seen from FIG. 19, the shank of pin 102 extends across passage 82. Thus, in the retracted position, it is not possible to pass a tool along passage 82 to engage the head of screw or bolt 94.

Moving the pin 102 from the retracted position to the extended position is essentially as described in my earlier Australian patent no. 755111. Thus, relative rotation between the inner members and outer members causes the pin 102 to move from the retracted position shown in FIG. 19 to the extended position shown in FIG. 20, in which the pin 102 extends through slot 46 and into the bone surrounding the medullary canal. It will be appreciated that this relative rotation causes all of the pins in the transversely extending grooves of the inner members to be extended.

Figure 20:
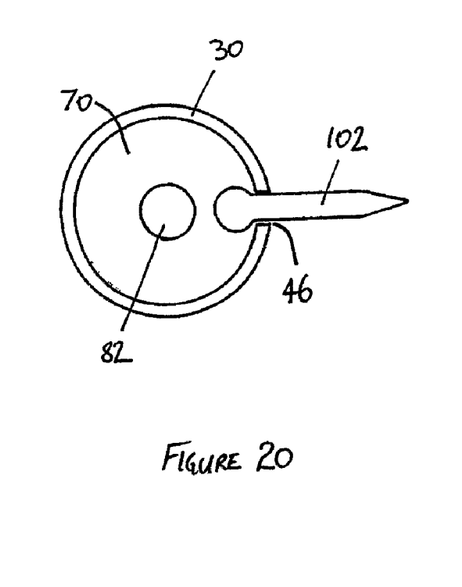
FIG. 20 shows a pin in the extended position in accordance with an embodiment of the present invention.

As best shown in FIG. 20, when the pins are moved to the extended position, the pins no longer extend across passage 82. Thus, once the pins have been extended and the device fixed into the medullary canal, it is possible to pass a tool along passage 82 to thereby engage and rotate screw or bolt 94.

When the device is assembled and the pins extended, the length of the device can be adjusted to that desired by inserting an appropriate tool into the head of the screw or bolt 94 and then turning the screw or bolt 94. Screw or bolt 94 can rotate relative to the proximal inner member without the relative longitudinal position between the head of the screw or bolt 94 and the proximal inner member 70 changing. However, as the distal inner member 50 is held against rotation relative to the proximal inner member 70 (by virtue of the tongue and projections arrangement described above), rotation of the screw or bolt 94 causes the threaded shank 96 to rotate with respect to the threaded passage 62 in the distal inner member 50. This causes the relative longitudinal positioning between the screw or bolt 94 and the distal inner member 50 to either extend or retract, depending upon the direction of rotation of the screw or bolt. This causes the relative longitudinal distance between the proximal inner member and the proximal outer member to be correspondingly altered.

Similarly, as the proximal outer member 30 and distal outer member 10 are prevented from rotating relative to each other (by virtue of the projecting tongues arrangement described above) and because the nails are extending through the proximal inner member 30 and distal inner member 10 to thereby maintain the longitudinal positioning of the distal inner member relative to the distal outer member and the proximal inner member relative to the proximal outer member, rotation of the screw or bolt 94 also causes relative longitudinal movement of the distal outer member 10 and proximal outer member 30. In this fashion, the overall length of the device can be lengthened or shortened.

The device in accordance with the present invention is particularly useful for the repair of the clavicle (collar bone), which at present is difficult to repair and is arguably the most commonly fractured bone in the body. The ability of the device to be shortened or contracted is particularly useful in that when the bones are aligned and the device inserted and the nails extended, the device can then be contracted to give compression of the bones at the fracture site, which is very desirable to aid in fracture repair.

The ability of the device to lengthen is particularly useful when there is a deficit of bone, for example, in the condition of hemi facial microsomia as described above in this specification.

Figure 17:
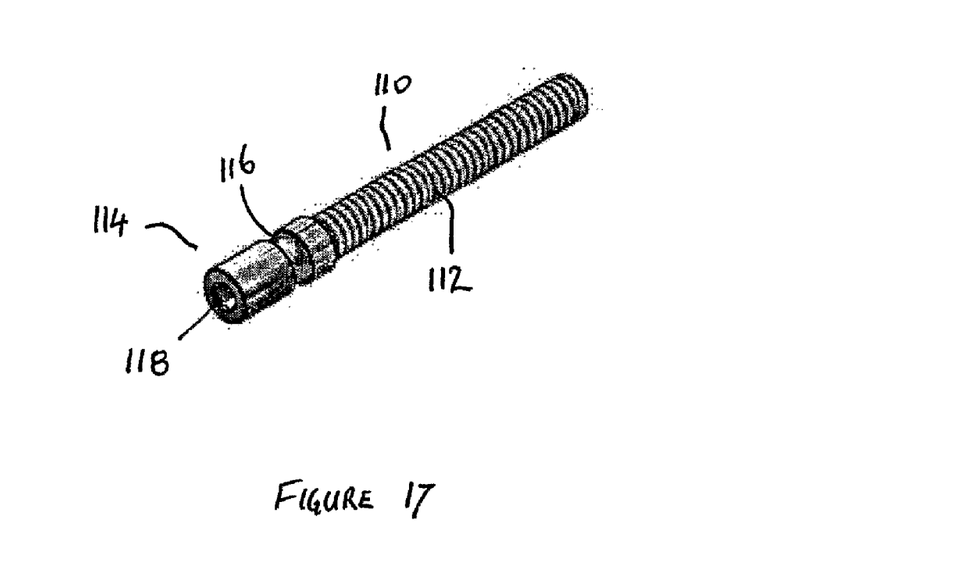
FIG. 17 shows a perspective view of another screw that can be used as the extension/retraction member in accordance with a further embodiment of the present invention.
Figure 18:
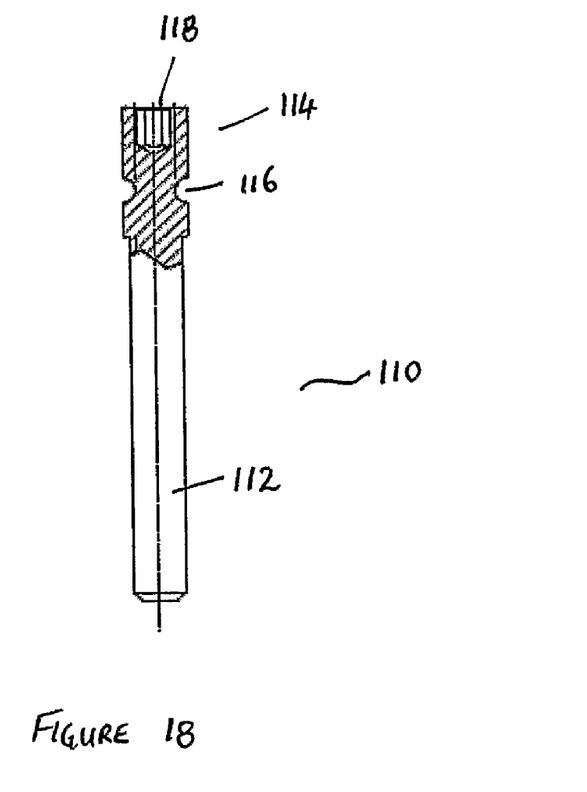
FIG. 18 is a side view, partly in cross-section, of the screw shown in FIG. 17.

The device in accordance with the present invention may be subject to variations and modifications. FIGS. 17 and 18 show one possible variation. In FIGS. 17 and 18 a screw or bolt 110 is used instead of screw or bolt 94 shown in FIGS. 15 and 16. Screw or bolt 110 includes a threaded shank 112 and a head portion 114. Head portion 114 includes a necked region 116. Necked region 116 comprises an area of reduced diameter surrounded by opposed shoulders. The head portion 114 also includes a hexagonal opening 118 for receiving an appropriately shaped tool.

Figure 12:
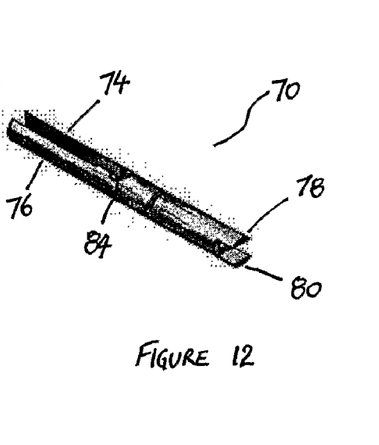
FIG. 12 shows a perspective view of the proximal inner member shown in FIG. 11, but looking from the opposite end.
Figure 13:
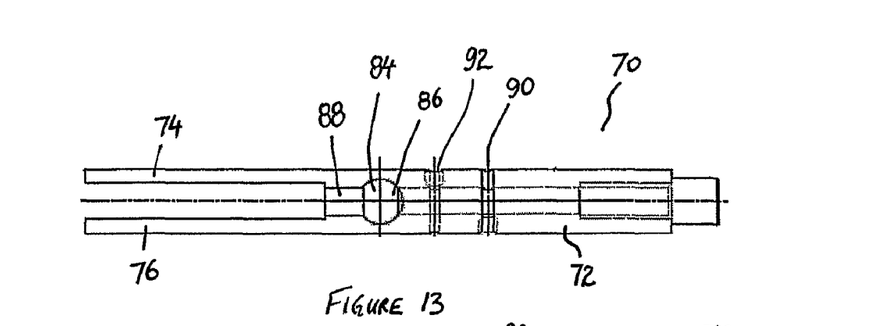
FIG. 13 shows an end view of the proximal inner member shown in FIGS. 11 and 12.

If screw or bolt 110 is used, the recess 84 of the proximal inner member 70 shown in FIGS. 12-14 is altered such that the recess has a profile that matches the head portion 114 of the screw or bolt 110.

Other modifications may also be made. For example, slot 64 formed in tongue 56 of distal inner member 50 may be replaced by a longer passage within tongue 56, which passage is effectively a blind bore in tongue 56. This passage may effectively be an extension of threaded passage 62.

The specific operation of the fixing pins may also be varied in accordance with the present invention. For example, the fixing pins may be operated as described in my co-pending international patent application no. PCT/AU03/01207, published as WO 2004/026158.

The device may also be provided with short tines 78, 80 to facilitate fitting of a handle of a tool, which can be of assistance in holding the device against rotation during extension or retraction of the pins. In some embodiments, both the proximal inner bar and proximal outer bar may be provided with similar tines that can be placed in alignment with each other. A locking cap having lugs that fit between and come into contact with the tines can be placed on the proximal end of the device such that the lugs lay across the common slots of the proximal end of the proximal inner bar and the proximal outer bar, thereby preventing any accidental retraction or extension (as the case may be) of the pins.

FIGS. 21-25 show various views of an intramedullary bone device in accordance with the present invention in a fully assembled state. The device shown in FIGS. 21-25 is generally similar to the device as shown in FIGS. 1-20, except that the device of FIGS. 21-25 includes six fixing pins instead of four. For convenience, like reference numerals will be used to denote like parts.

Figures 21, 22, 23:
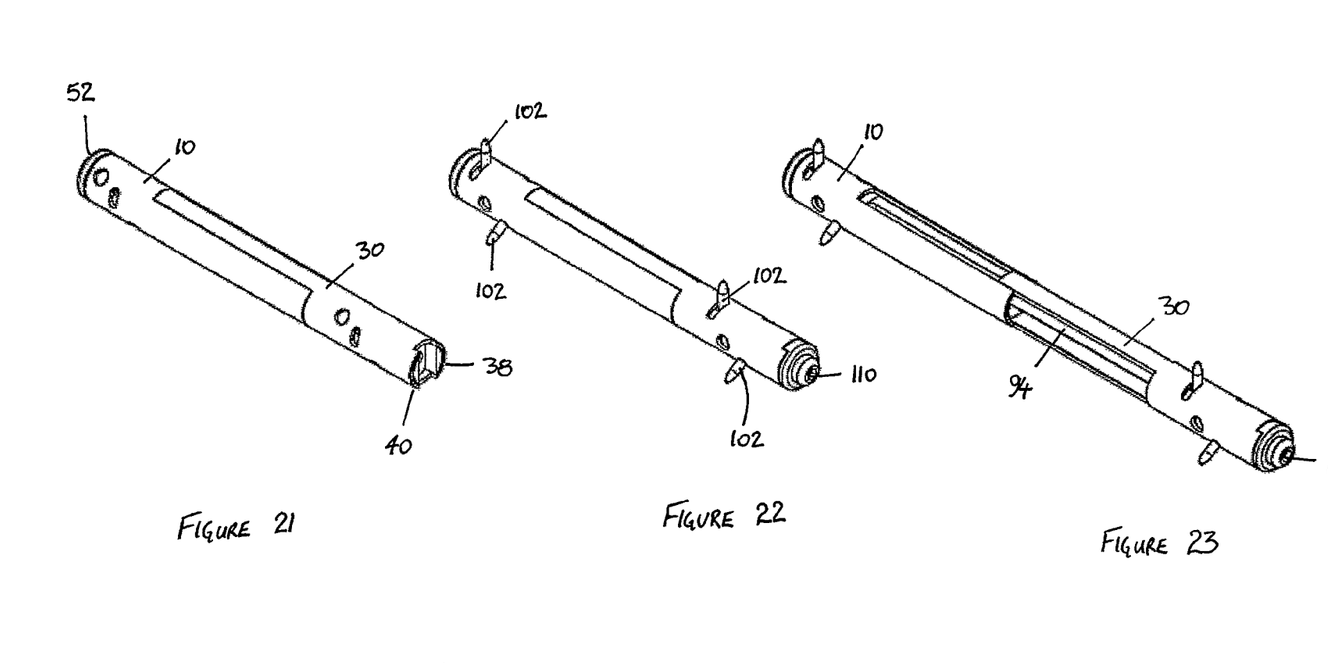
FIG. 21 shows an isometric view of a fully assembled device in accordance with an embodiment of the present invention, with the fixing pins in a retracted position and the device in its shortened configuration.
FIG. 22 shows the device of FIG. 21 with the fixing pins in an extended position.
FIG. 23 shows the device of FIG. 22 in its lengthened configuration.
Figure 24:
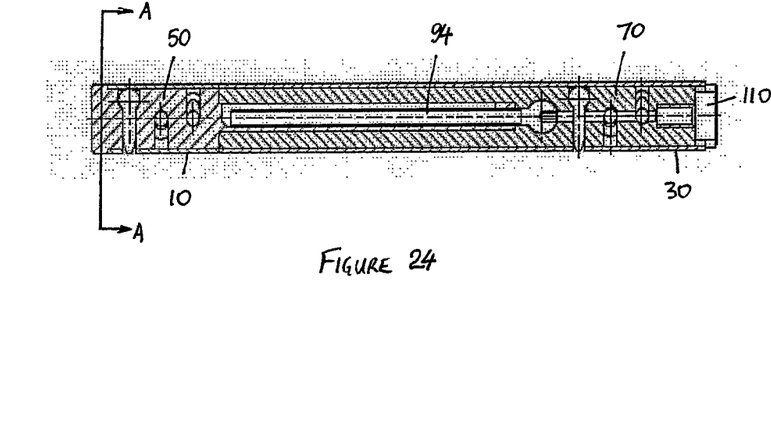
FIG. 24 is a cross-sectional side view of the device shown in FIG. 21.

FIG. 21 shows the device assembled in its shortened form with the pins in the retracted position. A cross-sectional view is shown in FIG. 24. Also shown in FIG. 24 is a locking cap 110 that is held in position between short tongues 38, 40 of the proximal outer member. Locking cap 110 includes a washer (not shown) and is used to seal the end of the device in instances where it is necessary to have the end of the device extend through the skin of the patient for at least a short period of time.

FIG. 22 shows an isometric view of the device in the shortened position but with the pins extended. FIG. 22 also shows the locking cap 110.

FIG. 23 shows an isometric view of the device shown in FIGS. 21 and 22 but in the lengthened position. The device is moved from the shortened position shown in FIG. 22 to the lengthened position shown in FIG. 23 by removing the locking cap 110 and the associated washer, inserting and engaging tool along the passage 82 through the proximal inner member and using the tool to rotate the screw 94. This causes the distal members to be moved away from the proximal members to thereby extend the length of the device.

Figure 25:
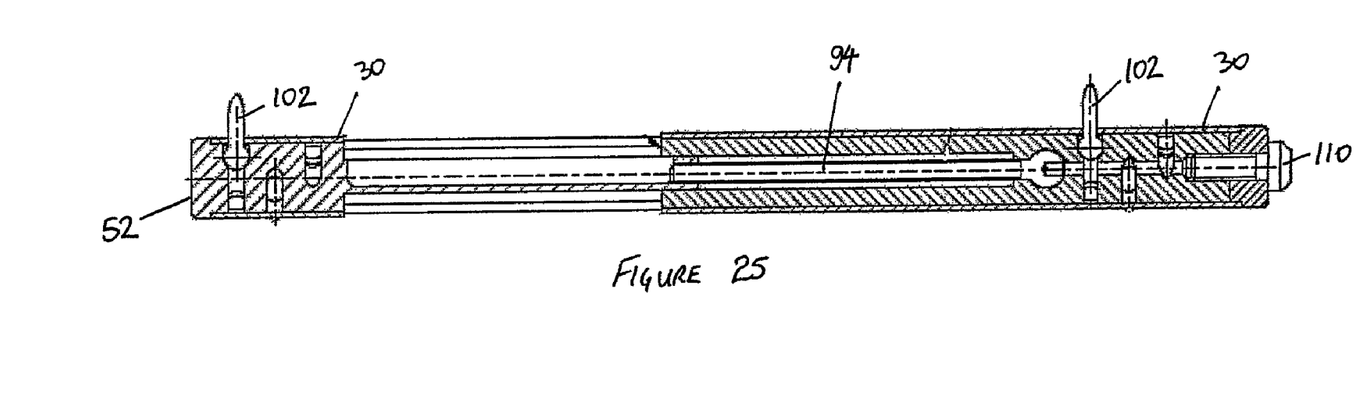
FIG. 25 is a cross-sectional side view of the device shown in FIG. 23.

FIG. 25 shows a cross-sectional side view of the device in the lengthened position.

Figure 26:
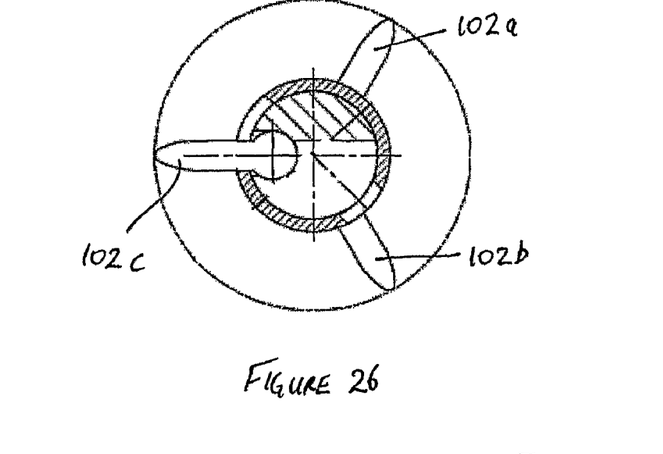
FIG. 26 is a cross-sectional end view taken along line A-A of FIG. 24.

FIG. 26 is a cross-sectional view taken along line A-A of FIG. 24. As can be seen from FIG. 26, the pins 102A, 102B and 102C are evenly radially distributed around the device (in this configuration, as there are three pins connecting the proximal members or the distal members, the pins are separated by 120°). If there are a different number of pins used, the angular spacing between the pins is suitably adjusted so that they remain evenly radially distributed.

Figure 27:
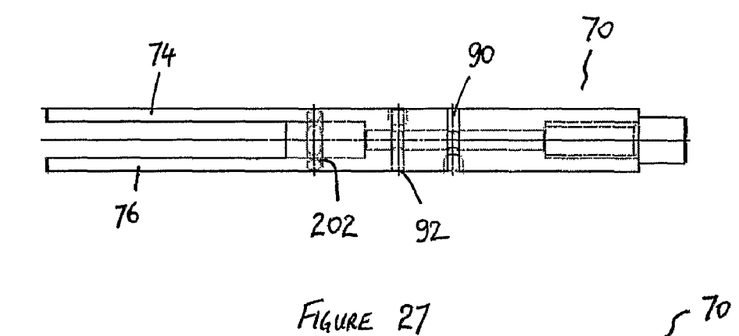
FIG. 27 is a side view of a proximal inner member suitable for use in a further embodiment of the present invention.
Figure 28:
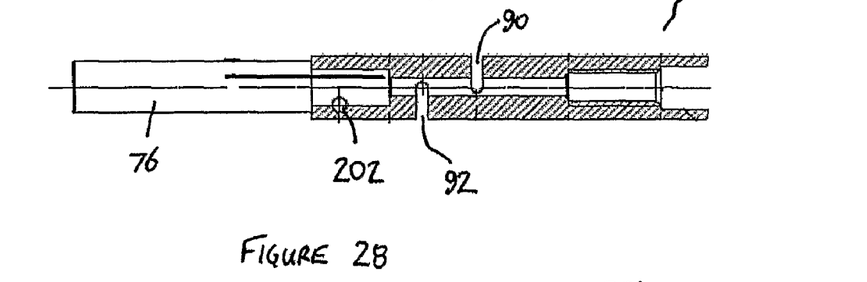
FIG. 28 is a cross sectional view of the proximal inner member shown in FIG. 27.
Figure 29:
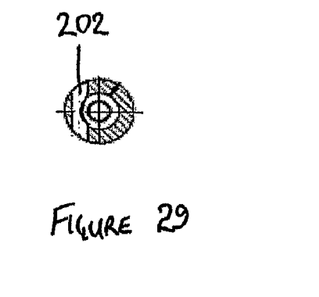
FIG. 29 shows a cross sectional end view taken along line B-B of FIG. 27.
Figure 30:
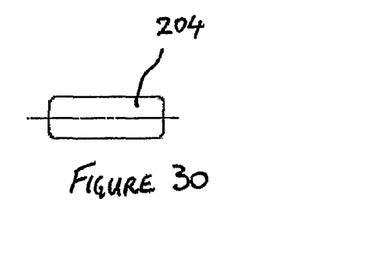
FIG. 30 shows a view of a pin for use with the inner proximal member shown in FIGS. 27 and 28.

The proximal inner bar shown in FIGS. 27 and 28 has a number of features in common with the proximal inner bar shown in FIGS. 11 to 14 and, for convenience, like parts will be designated by like reference numerals. The proximal inner bar shown in FIGS. 27 to 29 differs in that the recess 84 does not include a sperical enlargement, such as enlargement 86 shown in FIG. 13. Instead, a screw or bolt 110 as shown in FIGS. 17 and 18 is positioned in the recess 84 of the proximal inner bar 200 shown in FIGS. 27 and 28. A hole 202 is formed through the wall defining recess 84 and a pin 204 (shown in FIG. 30) is inserted into the hole 202 after the screw or bolt 110 is inserted into recess 84. The pin 204 fits into region 116 of screw or bolt 110 and thus acts to retain the longitudinal positioning of the screw or bolt relative to the proximal inner bar whilst at the same time allowing relative rotation therebetween.

Those skilled in the art will appreciate that the present invention may be subject to variations and modifications other than those specifically described. It will be appreciated that the present invention encompasses all such variations and such modifications that fall within its spirit and scope.

What is claimed is:

1. An intramedullary bone device comprising a distal outer member having at least one opening in a wall thereof, a proximal outer member for positioning in substantial axial alignment with the distal outer member, the proximal outer member having at least one opening in a wall thereof, said distal outer member having a passage therein, said proximal outer member having a passage therein, a distal inner member sized to be slideably received within the passage of the distal outer member, a proximal inner member sized to be slideably received within the passage of the proximal outer member, extension/retraction means being selectively operable to selectively alter the relative longitudinal positioning between the distal inner member and the proximal inner member, and pins movable between a retracted position and extended position, wherein the pins extend through the at least one opening in the distal and proximal outer members to fix the device to a bone during use, wherein rotation of the extension/retraction means in a first direction causes shortening of the device and rotation of the extension/retraction means in a second direction causes lengthening of the device and wherein at least one of the pins extends across a passage extending through the proximal inner member when the at least one pin is in the retracted position to prevent insertion of a tool through the passage of the proximal inner member and when the at least one pin is moved to the extended postion, the at least one pin no longer extends across the passage in the proximal inner member, thereby allowing a tool to be inserted along the passage to operate the extension/retraction means.

2. The device as claimed in claim 1 wherein relative axial orientation of the extended pins in both the proximal outer member and distal outer member is maintained during lengthening and shortening.

3. The device as claimed in claim 1 wherein the extension/retraction means is freely rotatable relative to one of the proximal or distal inner members and operates such that rotation alters the relative longitudinal position of the other of the proximal or distal inner members.

4. The device as claimed in claim 3 wherein the extension/retraction means is freely rotatable relative to one of the proximal or distal inner members whilst retaining its longitudinal position relative to that inner member, and rotation of the extension/retraction means alters the relative longitudinal position between the extension/retraction means and the other of the proximal or distal inner members.

5. The device as claimed in claim 4 wherein the extension/retraction means and the distal inner member are provided with a projection and groove arrangement, or interengaging ramps, to cause longitudinal movement between the extension/retraction means and the distal inner member upon rotation of the extension/retraction means.

6. The device as claimed in claim 4 wherein the proximal inner member includes a passage extending therethrough such that a tool can be inserted into the proximal inner member to engage with the extension/retraction means to thereby rotate the extension/retraction means.

7. The device as claimed in claim 4 wherein the extension/retraction means comprises a screw or bolt having a threaded shank threadably engaged with the distal inner member and a head positioned within a complementarily shaped recess in the proximal inner member such that the head can rotate relative to the proximal inner member and resist removal from the recess by application of a longitudinal force.

8. The device as claimed in claim 7 wherein the extension/retraction means comprises the screw and the head defines at least one shoulder that engages with an opposed shoulder formed in the recess of the proximal inner member.

9. The device as claimed in claim 7 wherein the head of the screw includes at least one neck region of reduced diameter that engages with a complementary shaped projection in the recess in the proximal inner member.

10. The device as claimed in claim 7 wherein the recess in the proximal inner member includes a shank receiving portion and a head receiving portion.

11. The device as claimed in claim 7 wherein the head of the extension/retraction means is located at one end of the proximal inner member and the shank extends through the proximal inner member into engagement with the distal inner member.

12. The device as claimed in claim 1 wherein the distal inner member and the proximal inner member are arranged such that relative rotational movement therebetween is avoided.

13. The device as claimed in claim 12 wherein one of the proximal or distal inner members is provided with a flat land that engages with a projection extending from the other of the proximal or distal inner members.

14. The device as claimed in claim 13 wherein one of the proximal or distal inner members is provided with two flat lands that engage with two projections extending from the other inner member.

15. The device as claimed in claim 12 wherein one of the proximal or distal inner members includes a keyway that engages with a key formed on the other of the proximal or distal inner members.

16. The device as claimed in claim 1 wherein the proximal and distal outer members are arranged such that relative rotational movement therebetween is avoided.

17. The device as claimed in claim 16 wherein the proximal and distal outer members have one or more tongues that interfit with complementary tongues on the other of the proximal or distal outer members.

18. The device as claimed in claim 17 wherein the proximal outer member has two tongues extending from an end that interlock with two tongues extending from the distal outer member to thereby prevent relative rotation therebetween.

19. The device as claimed in claim 1 wherein, when in the retracted position, the pins do not extend beyond an outer surface of the outer members and in the extended position, the pins extend through the one or more openings in the walls of the outer members and are adapted to extend into the bone surrounding the medullary canal.

20. The device as claimed in claim 1 wherein the pins are arranged in transverse grooves on the inner members and rotation of the inner members relative to the outer members causes the pins to extend through the openings in the outer members and the pins are adapted to extend into the bone surrounding the medullary canal.

21. A method for using a device as claimed in claim 1, the method including the steps of inserting the device into a medullary canal of a bone, moving the pins to an extended position to thereby fix the device to the bone surrounding the medullary canal such that the distal members are fixed to the bone on one side of a break in the bone and the proximal members are fixed to the bone on another side of a break in the bone, and selectively lengthening or shortening the device by operation of the extension/retraction means.

22. An intramedullary bone device comprising a distal outer member having at least one opening in a wall thereof, a proximal outer member for positioning in substantial axial alignment with the distal outer member, the proximal outer member having at least one opening in a wall thereof, said distal outer member having a passage therein, said proximal outer member having a passage therein, a distal inner member sized to be slideably received within the passage of the distal outer member, a proximal inner member sized to be slideably received within the passage of the proximal outer member, extension/retraction means being selectively operable to selectively alter the relative longitudinal positioning between the distal inner member and the proximal inner member, and pins movable between a retracted postion and an extended position, wherein the pins extend through the at least one opening in the distal and the proximal outer members to fix the device to a bone during use, wherein the distal inner member and proximal inner member are constrained against rotation relative to each other and the distal out member and the proximal outer member are constrained against rotation relative to each other, wherein rotation of the extension/retraction means in a first direction causes shortening of the device and rotation of the extension/retraction means in a second direction causes lengthening of the device and wherein at least one of the pins extends across a passage extending through the proximal inner member when the at least one pin is in the retracted position to prevent insertion of a tool through the passage of the proximal inner member and when the at least one pin is moved to the extended position, the at least one pin no longer extends across the passage in the proximal inner member, thereby allowing a tool to be inserted along the passage to operate the extension/retraction means.

* * * * *